United States Patent
Huang et al.

(10) Patent No.: US 12,099,044 B2
(45) Date of Patent: *Sep. 24, 2024

(54) PORTABLE ELECTRONIC DEVICE FOR USE IN DIFFERENT ORIENTATIONS

(71) Applicant: RADIANT INNOVATION INC., Hsinchu County (TW)

(72) Inventors: Yu-Chien Huang, Hsinchu (TW); Chien-Chang Liao, Hsinchu (TW)

(73) Assignee: RADIANT INNOVATION INC., Hsinchu County (TW)

( * ) Notice: Subject to any disclaimer, the term of this patent is extended or adjusted under 35 U.S.C. 154(b) by 408 days.

This patent is subject to a terminal disclaimer.

(21) Appl. No.: 17/577,377

(22) Filed: Jan. 18, 2022

(65) Prior Publication Data
US 2023/0228724 A1 Jul. 20, 2023

(51) Int. Cl.
*G01N 33/00* (2006.01)
*F24F 11/89* (2018.01)
*G06F 1/16* (2006.01)
*G06T 13/80* (2011.01)

(52) U.S. Cl.
CPC .......... *G01N 33/004* (2013.01); *F24F 11/89* (2018.01); *G01N 33/0063* (2013.01); *G01N 33/0075* (2013.01); *G06F 1/1694* (2013.01); *G06T 13/80* (2013.01); *G06F 2200/1637* (2013.01)

(58) Field of Classification Search
None
See application file for complete search history.

(56) References Cited

U.S. PATENT DOCUMENTS

| | | | | |
|---|---|---|---|---|
| 5,758,267 A | * | 5/1998 | Pinder | H04B 1/401 341/20 |
| 9,612,195 B1 | * | 4/2017 | Friedman | G08B 21/14 |
| 2003/0157971 A1 | * | 8/2003 | Lieu | H01H 25/041 455/566 |
| 2006/0215052 A1 | * | 9/2006 | Nagaoka | H04N 23/631 348/E5.025 |
| 2006/0240875 A1 | * | 10/2006 | Miyazawa | G06F 3/017 455/566 |

(Continued)

*Primary Examiner* — Lisa M Caputo
*Assistant Examiner* — Cynthia L Davis
(74) *Attorney, Agent, or Firm* — Li & Cai Intellectual Property Office

(57) ABSTRACT

A portable electronic device for use in different orientations includes a signal control module, a key control module, an information display module, and a position detection module. The key control module includes a plurality of functional switches and functional keys. The signal control module has a plurality of key function execution commands respectively corresponding to the functional keys. The position detection module is configured for detecting a placement orientation of the portable electronic device. When the portable electronic device is rotated to change the placement orientation of the information display module, a screen orientation of an information display image provided by the information display module is changed following a change of the placement orientation of the information display module, and a corresponding relationship between the functional switch and the key function execution command is changed following the change of the placement orientation of the information display module.

10 Claims, 13 Drawing Sheets

(56) References Cited

U.S. PATENT DOCUMENTS

| | | | |
|---|---|---|---|
| 2007/0093281 A1* | 4/2007 | Park | H04M 1/0233 455/575.4 |
| 2012/0001942 A1* | 1/2012 | Abe | G09G 5/003 345/650 |
| 2015/0221287 A1* | 8/2015 | Badawiyeh | G06F 1/1626 345/659 |
| 2018/0335380 A1* | 11/2018 | Schmidt | H04N 23/11 |

* cited by examiner

PORTABLE ELECTRONIC DEVICE FOR USE IN DIFFERENT ORIENTATIONS

FIELD OF THE DISCLOSURE

The present disclosure relates to a portable electronic device, and more particularly to a portable electronic device suitable for being used in different orientations.

BACKGROUND OF THE DISCLOSURE

A conventional portable monitor can provide relevant information for a user, but still has room for improvement in the related art.

SUMMARY OF THE DISCLOSURE

In response to the above-referenced technical inadequacy, the present disclosure provides a portable electronic device for use in different orientations.

In one aspect, the present disclosure provides a portable electronic device for use in different orientations, which includes a device main body, a signal control module, a key control module, an information display module, and a position detection module. The signal control module is disposed inside the device main body. The key control module is disposed on the device main body and electrically connected to the signal control module. The information display module is disposed on the device main body and electrically connected to the signal control module, for providing a plurality of information display images. The position detection module is disposed inside the device main body and electrically connected to the signal control module, for detecting a placement orientation of the portable electronic device so as to obtain an orientation signal. The key control module includes a plurality of functional switches electrically connected to the signal control module, and a plurality of functional keys respectively and selectively contacting the functional switches, and the information display module includes an information displayer for displaying the information display images. The signal control module has a plurality of key function execution commands respectively corresponding to the functional keys, and the key function execution commands at least includes a top key function execution command, a bottom key function execution command, a left key function execution command, and a right key function execution command.

More particularly, when the device main body is rotated so as to change the placement orientation of the information display module, a screen orientation of the information display image provided by the information display module is changed following a change of the placement orientation of the information display module, and a corresponding relationship between the functional switch and the key function execution command is changed following the change of the placement orientation of the information display module. When the placement orientation of the information display module is changed through rotation of the device main body, a topmost one of the functional switches on the device main body is defined as a top functional switch for executing the top key function execution command, a bottommost one of the functional switches on the device main body is defined as a bottom functional switch for executing the bottom key function execution command, a leftmost one of the functional switches on the device main body is defined as a left functional switch for executing the left key function execution command, and a rightmost one of the functional switches on the device main body is defined as a right functional switch for executing the right key function execution command. When the placement orientation of the information display module is changed through rotation of the device main body, a topmost one of the functional keys on the device main body is defined as a top functional key for executing the top key function execution command by pressing the top functional switch, a bottommost one of the functional keys on the device main body is defined as a bottom functional key for executing the bottom key function execution command by pressing the bottom functional switch, a leftmost one of the functional keys on the device main body is defined as a left functional key for executing the left key function execution command by pressing the left functional switch, and a rightmost one of the functional keys on the device main body is defined as a right functional key for executing the right key function execution command by pressing the right functional switch.

In another aspect, the present disclosure provides a portable electronic device for use in different orientations, which includes a signal control module, a key control module, an information display module, and a position detection module. The key control module is electrically connected to the signal control module. The information display module is electrically connected to the signal control module, for providing a plurality of information display images. The position detection module is electrically connected to the signal control module, for detecting a placement orientation of the portable electronic device so as to obtain an orientation signal. The key control module includes a plurality of functional switches electrically connected to the signal control module, and a plurality of functional keys respectively and selectively contacting the functional switches, and the information display module includes an information displayer for displaying the information display images. The signal control module has a plurality of key function execution commands respectively corresponding to the functional keys, and the key function execution commands at least includes a top key function execution command, a bottom key function execution command, a left key function execution command, and a right key function execution command. When the portable electronic device is rotated so as to change the placement orientation of the information display module, a screen orientation of the information display image provided by the information display module is changed following a change of the placement orientation of the information display module, and a corresponding relationship between the functional switch and the key function execution command is changed following the change of the placement orientation of the information display module.

Therefore, in the portable electronic device provided by the present disclosure, by virtue of the key control module being electrically connected to the signal control module, the information display module being electrically connected to the signal control module, for providing a plurality of information display images, the position detection module being electrically connected to the signal control module, for detecting a placement orientation of the portable electronic device so as to obtain an orientation signal, the key control module including a plurality of functional switches electrically connected to the signal control module, and a plurality of functional keys respectively and selectively contacting the functional switches, and the information display module including an information displayer for displaying the information display images, and the signal control module having a plurality of key function execution commands respectively corresponding to the functional keys, and the key function execution commands at least including a top key function execution command, a bottom key function execution command, a left key function execution command, and a right key function execution command, when the portable electronic device is rotated so as to change the placement orientation of the information display module, a screen orientation of the information display image provided by the information display module is changed following a change of the placement orientation of the information display module, and a corresponding relationship between the functional switch and the key function execution command is also changed following the change of the placement orientation of the information display module.

These and other aspects of the present disclosure will become apparent from the following description of the embodiment taken in conjunction with the following drawings and their captions, although variations and modifications therein may be affected without departing from the spirit and scope of the novel concepts of the disclosure.

BRIEF DESCRIPTION OF THE DRAWINGS

The described embodiments may be better understood by reference to the following description and the accompanying drawings, in which.

DETAILED DESCRIPTION OF THE EXEMPLARY EMBODIMENTS

Figure 1:
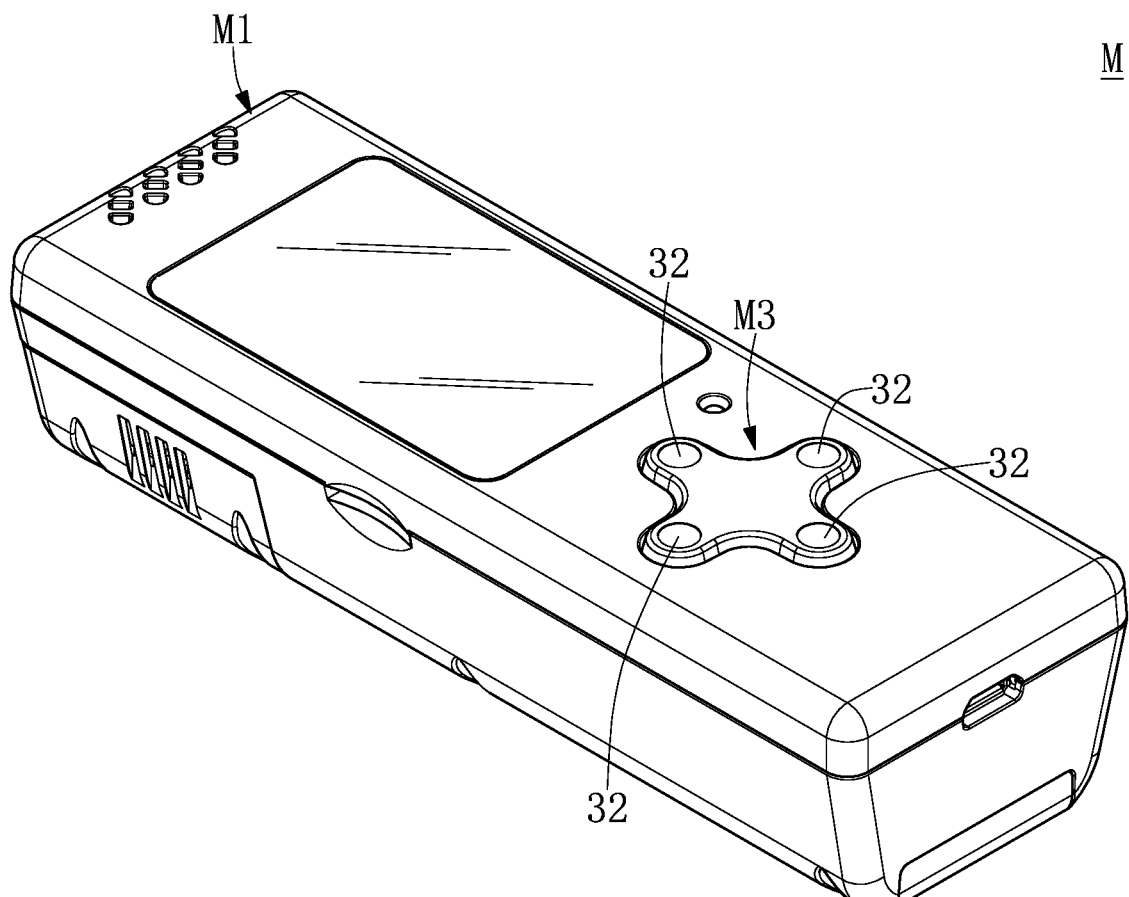
FIG. 1 is a schematic perspective view of a portable electronic device according to the present disclosure.

The present disclosure is more particularly described in the following examples that are intended as illustrative only since numerous modifications and variations therein will be apparent to those skilled in the art. Like numbers in the drawings indicate like components throughout the views. As used in the description herein and throughout the claims that follow, unless the context clearly dictates otherwise, the meaning of "a", "an", and "the" includes plural reference, and the meaning of "in" includes "in" and "on". Titles or subtitles can be used herein for the convenience of a reader, which shall have no influence on the scope of the present disclosure.

The terms used herein generally have their ordinary meanings in the art. In the case of conflict, the present document, including any definitions given herein, will prevail. The same thing can be expressed in more than one way. Alternative language and synonyms can be used for any term(s) discussed herein, and no special significance is to be placed upon whether a term is elaborated or discussed herein. A recital of one or more synonyms does not exclude the use of other synonyms. The use of examples anywhere in this specification including examples of any terms is illustrative only, and in no way limits the scope and meaning of the present disclosure or of any exemplified term. Likewise, the present disclosure is not limited to various embodiments given herein. Numbering terms such as "first", "second" or "third" can be used to describe various components, signals or the like, which are for distinguishing one component/signal from another one only, and are not intended to, nor should be construed to impose any substantive limitations on the components, signals or the like.

First Embodiment

Referring to FIG. 1 to FIG. 8, a first embodiment of the present disclosure provides a portable electronic device M (such as a portable monitor) suitable for (or adapted to) different use orientations (or placement orientation), which includes a device main body M1, a signal control module M2, a key control module M3, an information display module M4, and a position detection module M5.

Figure 3:
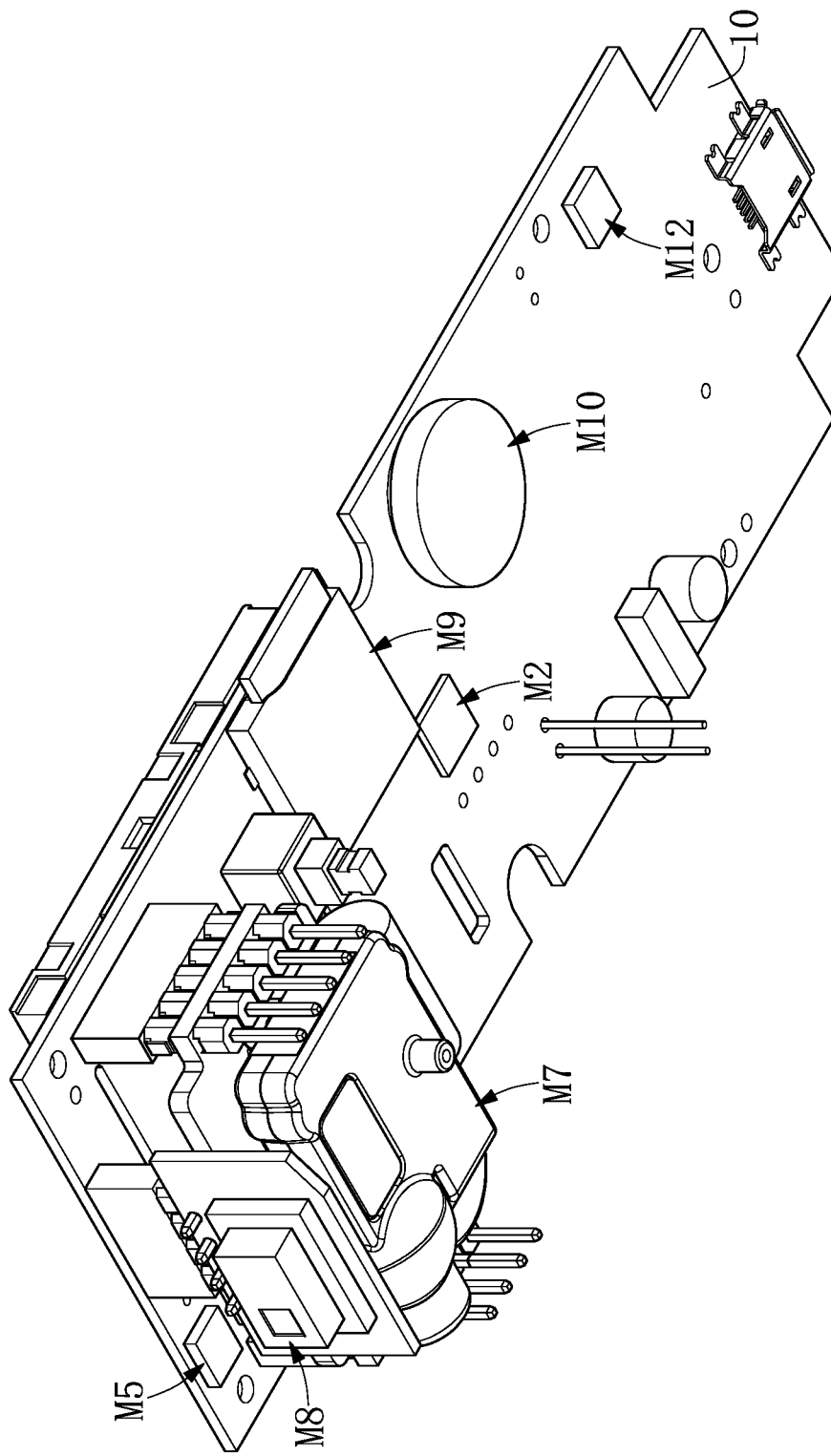
FIG. 3 is another schematic perspective view of the portable electronic device after the device casing of the portable electronic device is removed according to the present disclosure.
Figure 4:
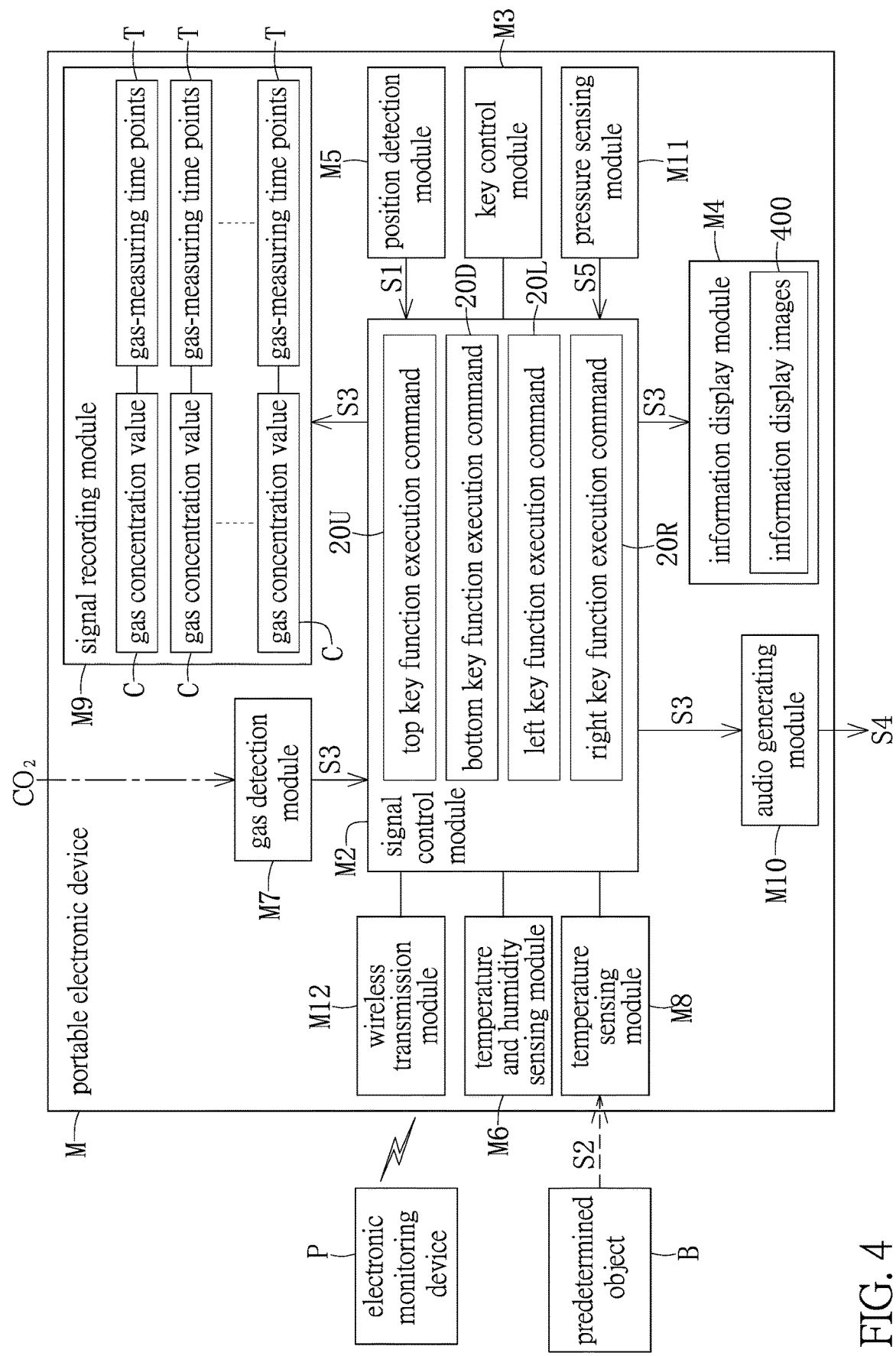
FIG. 4 is a functional block diagram of the portable electronic device according to the present disclosure.
Figure 5:
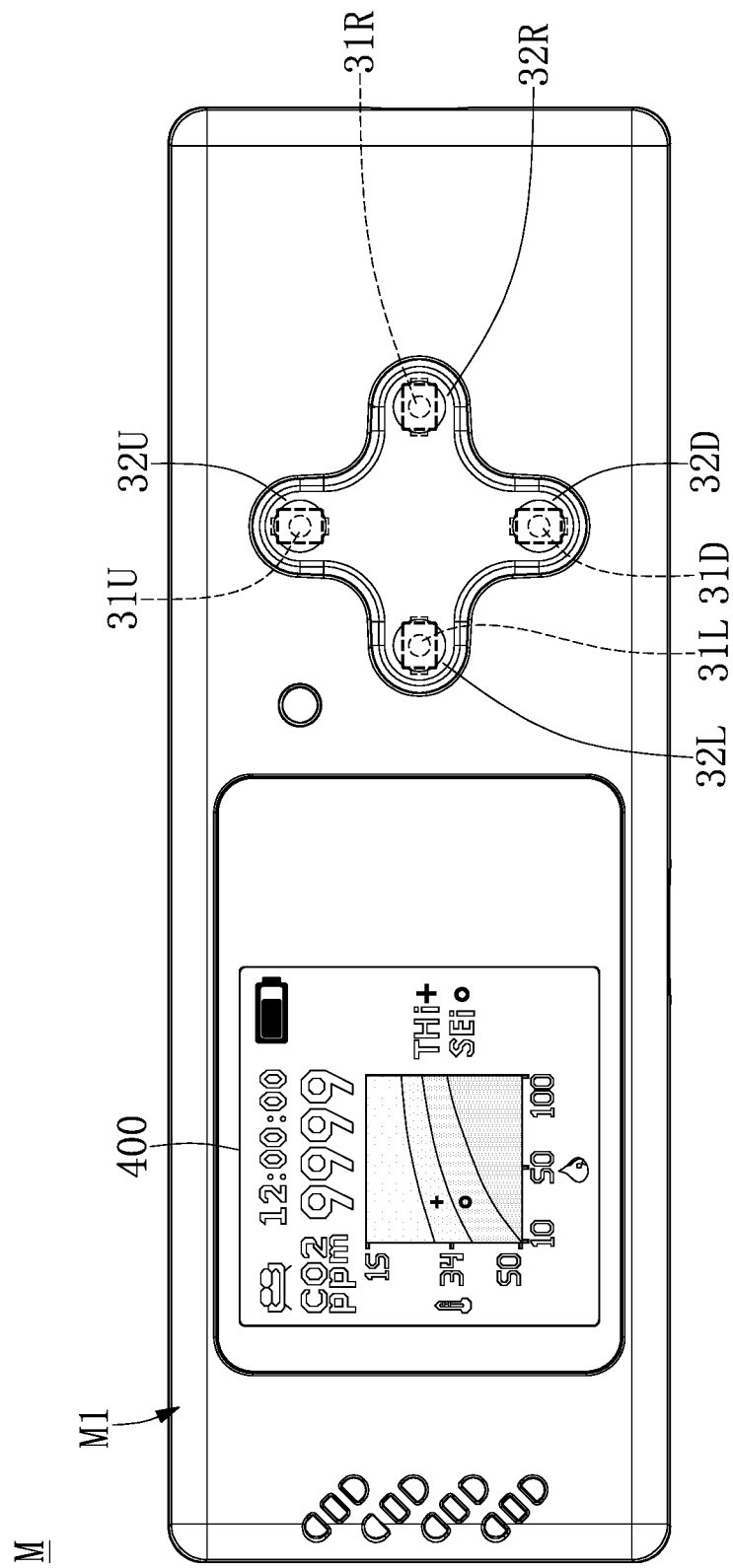
FIG. 5 is a schematic view of a first placement orientation of the portable electronic device according to a first embodiment of the present disclosure.
Figure 6:
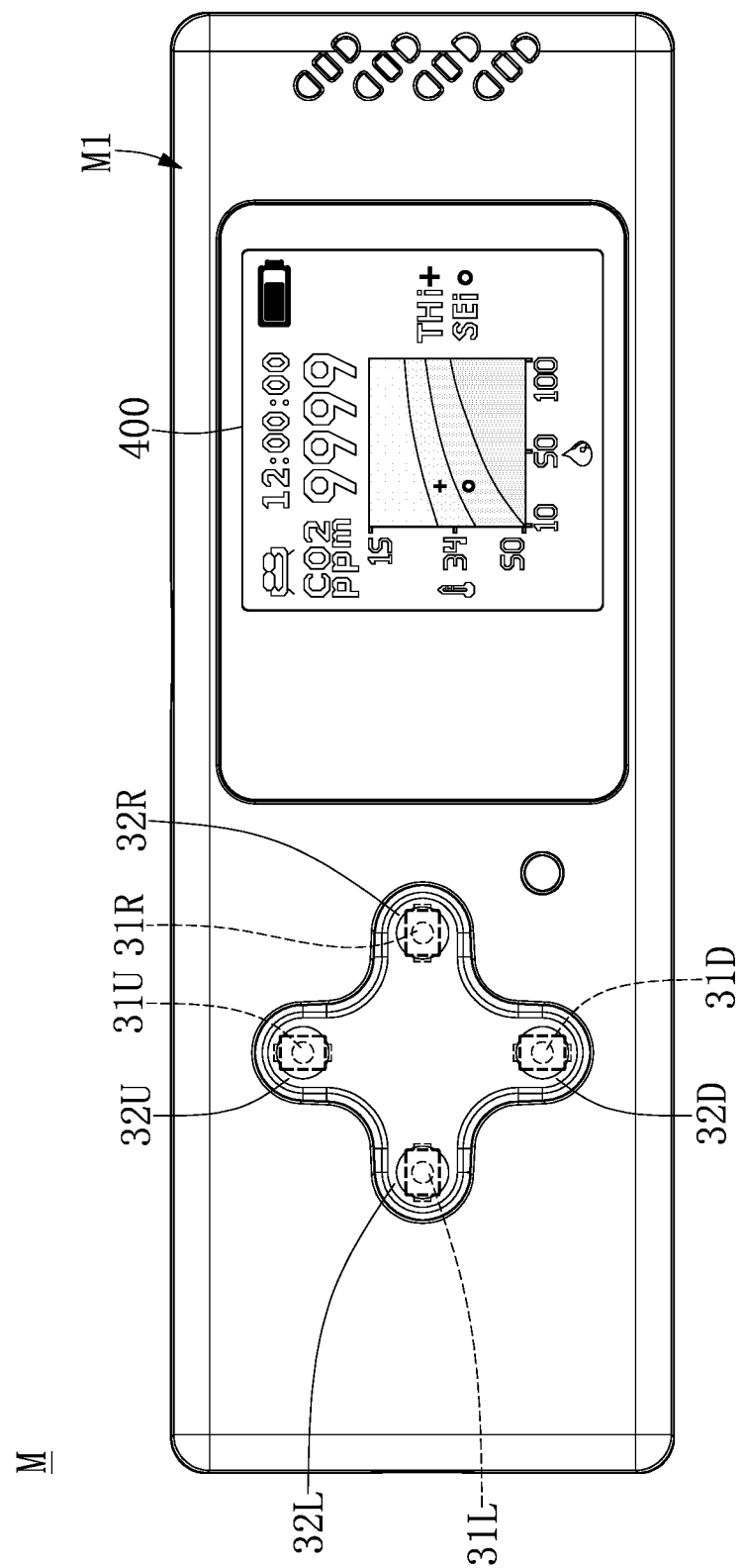
FIG. 6 is a schematic view of a second placement orientation of the portable electronic device according to the first embodiment of the present disclosure.
Figure 7:
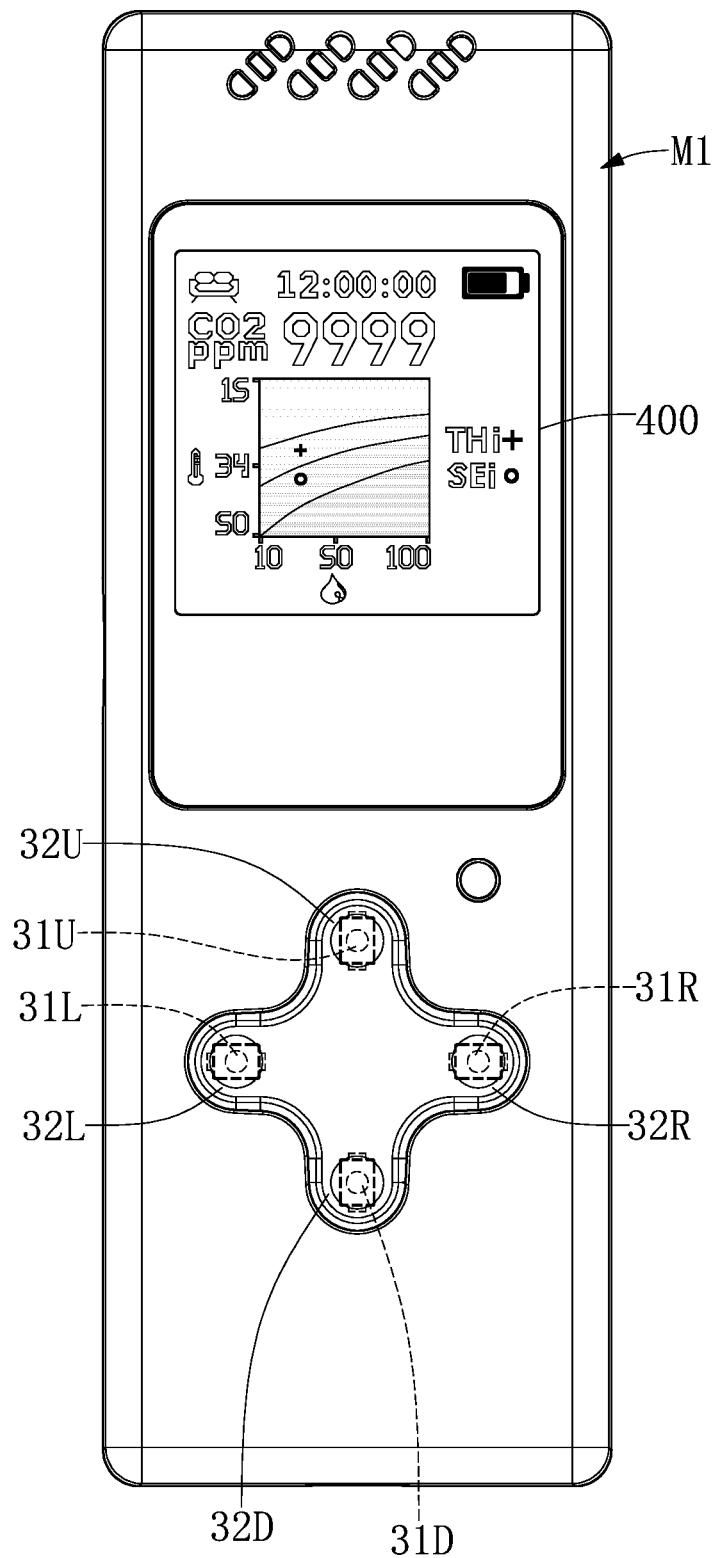
FIG. 7 is a schematic view of a third placement orientation of the portable electronic device according to the first embodiment of the present disclosure.
Figure 8:
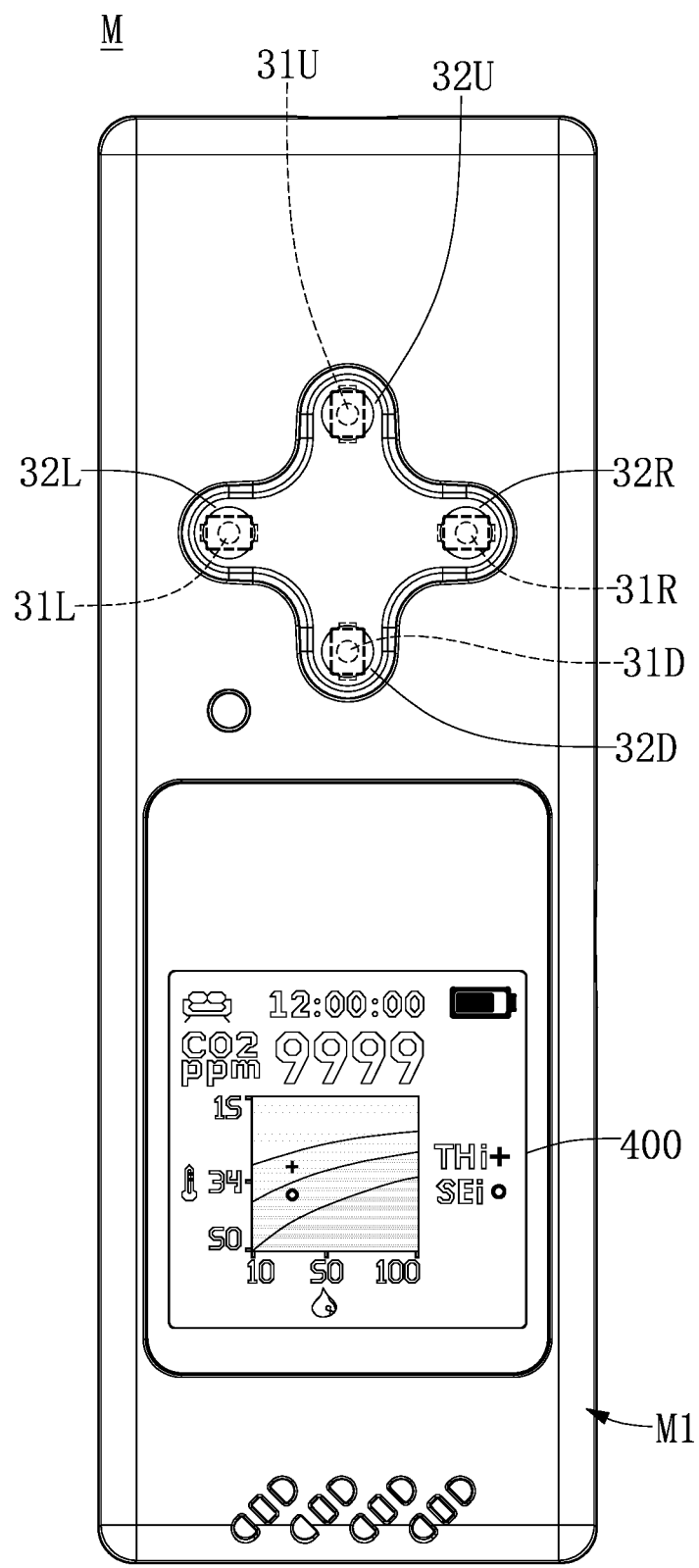
FIG. 8 is a schematic view of a fourth placement orientation of the portable electronic device according to the first embodiment of the present disclosure.

More particularly, referring to FIG. 1, FIG. 3 and FIG. 4, the signal control module M2 is disposed inside the device main body M1. In addition, the signal control module M2 has a plurality of key function execution commands, and the key function execution commands at least include a top key function execution command 20U, a bottom key function execution command 20D, a left key function execution command 20L, and a right key function execution command 20R. For example, the device main body M1 includes a device casing (not labeled) and at least one circuit substrate 10 disposed inside the device casing, and the signal control module M2 is disposed on the circuit substrate 10 and electrically connected to the circuit substrate 10. In addition, the signal control module M2 can be a central processing unit (CPU), a digital signal process (DSP), a microprocessor unit (MPU), or a micro control unit (MCU), etc. However, the aforementioned details are disclosed for exemplary purposes only, and are not meant to limit the scope of the present disclosure.

Figure 2:
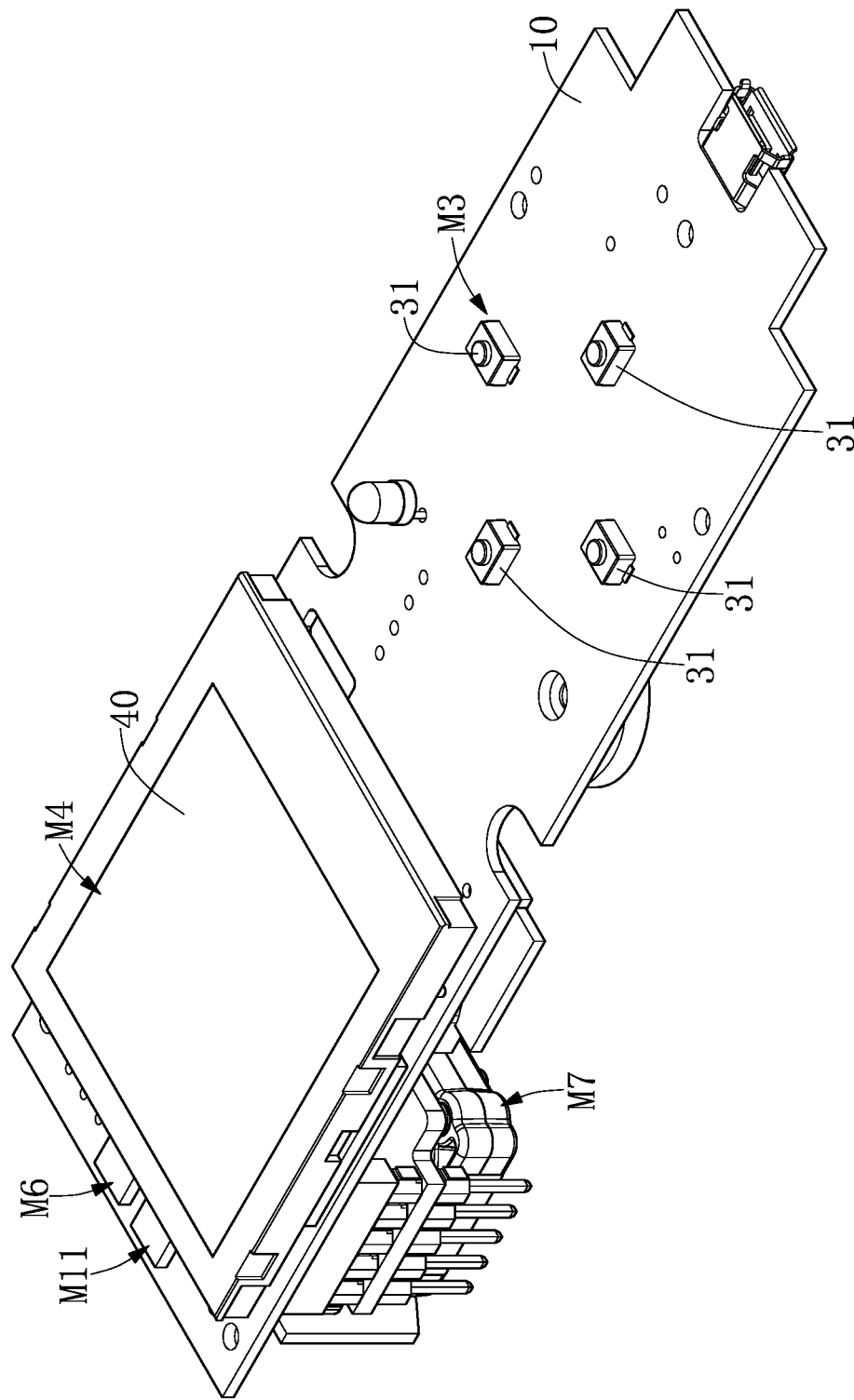
FIG. 2 is a schematic perspective view of the portable electronic device after a device casing of the portable electronic device is removed according to the present disclosure.

More particularly, referring to FIG. 1, FIG. 2 and FIG. 4, the key control module M3 is disposed on the device main body M1 and electrically connected to the signal control module M2, and the key control module M3 includes a plurality of functional switches 31 electrically connected to the signal control module M2, and a plurality of functional keys 32 respectively and selectively contacting (or pressing) the functional switches 31. In addition, the key function execution commands of the signal control module M2 can respectively correspond to the functional keys 32. For example, the functional switches 31 are disposed on the circuit substrate 10 and electrically connected to the circuit substrate 10, and the functional keys 32 can be movably disposed on the device main body M1. Moreover, the functional keys 32 can be separate from each other, or combined to form a single key structure (as shown in FIG. 1), and no character or pattern is formed on the functional key or a peripheral area around the functional key (that is to say, a function of each of the functional keys 32 is changeable according to different use orientations, so that the functional key 32 does not need to be defined by any character or pattern). However, the aforementioned details are disclosed for exemplary purposes only, and are not meant to limit the scope of the present disclosure.

More particularly, referring to FIG. 2 and FIG. 4, the information display module M4 is disposed on the device main body M1 and electrically connected to the signal control module M2, and the information display module M4 includes an information displayer 40 for displaying the information display images 400. For example, the information display module M4 is disposed on the circuit substrate 10 and electrically connected to the circuit substrate 10, and the information display module M4 can be protected by a transparent protection layer (not labeled) provided by the device main body M1. In addition, the information display module M4 can be a liquid-crystal display (LCD) or any display device for displaying information. However, the aforementioned details are disclosed for exemplary purposes only, and are not meant to limit the scope of the present disclosure.

More particularly, referring to FIG. 3 and FIG. 4, the position detection module M5 is disposed inside the device main body M1 and electrically connected to the signal control module M2, and the position detection module M5 can be configured for detecting a placement orientation (or a use orientation) of the portable electronic device M so as to obtain an orientation signal S1. For example, the position detection module M5 is disposed on the circuit substrate 10 and electrically connected to the circuit substrate 10, and the position detection module M5 can be an acceleration transducer, a gyroscope, or any position detecting chip for detecting the placement orientation of the portable electronic device M so as to obtain the orientation signal S1, and transmitting the orientation signal S1 to the signal control module M2. However, the aforementioned details are disclosed for exemplary purposes only, and are not meant to limit the scope of the present disclosure.

More particularly, referring to FIG. 4 to FIG. 8, when the device main body M1 is turned (for example, the device main body M1 that is turned by 90 degrees as shown in any one of FIG. 5 to FIG. 8 is detected by the position detection module M5) for changing a placement orientation (or a use orientation) of the information display module M4, a screen orientation (i.e., a front screen orientation or a front viewing orientation, not an inverted screen orientation or an inclined screen orientation) of the information display image 400 provided by the information display module M4 is changed following a change of the placement orientation (or the use orientation) of the information display module M4, and a corresponding relationship between the functional switch 31 and the key function execution command 20 (i.e., the corresponding relationship between a corresponding one of the functional switch 31 and a corresponding one of the key function execution commands 20) is also changed following the change of the placement orientation (or the use orientation) of the information display module M4. That is to say, when the placement orientation of the information display module M4 is changed through rotation of the device main body M1 as shown in any one of FIG. 5 to FIG. 8, not only the screen orientation of the information display image 400 provided by the information display module M4 can be changed following the change of the placement orientation of the information display module M4, but also the function of each of the functional switches 31 can be changed following the change of the placement orientation of the information display module M4.

For example, referring to FIG. 2 and FIG. 4 to FIG. 8, when the placement orientation (or the use orientation) of the information display module M4 is changed through rotation of the device main body M1 (for example, the device main body M1 that is turned by 90 degrees as shown in any one of FIG. 5 to FIG. 8 is detected by the position detection module M5), a topmost one of the functional switches 31 (or a topmost functional switch 31) on the device main body M1 can be defined as a top functional switch 31U for executing the top key function execution command 20U, a bottommost one of the functional switches 31 (or a bottommost functional switch 31) on the device main body M1 can be defined as a bottom functional switch 31D for executing the bottom key function execution command 20D, a leftmost one of the functional switches 31 (or a leftmost functional switch 31) on the device main body M1 can be defined as a left functional switch 31L for executing the left key function execution command 20L, and a rightmost one of the functional switches 31 (or a rightmost functional switch 31) on the device main body M1 can be defined as a right functional switch 31R for executing the right key function execution command 20R. However, the aforementioned details are disclosed for exemplary purposes only, and are not meant to limit the scope of the present disclosure.

For example, referring to FIG. 1 and FIG. 4 to FIG. 8, when the placement orientation (or the use orientation) of the information display module M4 is changed through rotation of the device main body M1 (for example, the device main body M1 that is turned by 90 degrees as shown in any one of FIG. 5 to FIG. 8 is detected by the position detection module M5), a topmost one of the functional keys 32 (or a topmost functional key 32) on the device main body M1 can be defined as a top functional key 32U for executing the top key function execution command 20U by pressing (or contacting) the top functional switch 31U, a bottommost one of the functional keys 32 (or a bottommost functional key 32) on the device main body M1 can be defined as a bottom functional key 32D for executing the bottom key function execution command 20D by pressing (or contacting) the bottom functional switch 31D, a leftmost one of the functional keys 32 (or a leftmost functional key 32) on the device main body M1 can be defined as a left functional key 32L for executing the left key function execution command 20L by pressing (or contacting) the left functional switch 31L, and a rightmost one of the functional keys 32 (or a rightmost functional key 32) on the device main body M1 can be defined as a right functional key 32R for executing the right key function execution command 20R by pressing (or contacting) the right functional switch 31R. However, the aforementioned details are disclosed for exemplary purposes only, and are not meant to limit the scope of the present disclosure.

For example, referring to FIG. 4 to FIG. 8, the top key function execution command 20U can be an upward selection command, the bottom key function execution command 20D can be a downward selection command, the left key function execution command 20L can be a mode switching command, and the right key function execution command 20R can be an enter confirmation command (or an enter command) Therefore, when the top functional key 32U is configured to press the top functional switch 31U so as to execute the upward selection command, a plurality of different functional areas (not shown) provided by the information display image 400 can be upwardly selected by the upward selection command (i.e., by pressing the top functional key 32U). When the bottom functional key 32D is configured to press the bottom functional switch 31D so as to execute the downward selection command, the different functional areas provided by the information display image 400 can be downwardly selected by the downward selection command (i.e., by pressing the bottom functional key 32D). When the left functional key 32L is configured to press the left functional switch 31L so as to execute the mode switching command, the information display images 400 can be selected by the mode switching command (i.e., by pressing the left functional key 32L) so as to display one of the information display images 400 on the information display module M4. When the right functional key 32R is configured to press the right functional switch 31R so as to execute the enter confirmation command, an enter confirmation signal (not shown) can be transmitted to the signal control module M2 by control of the enter confirmation command (i.e., by pressing the right functional key 32R). However, the aforementioned details are disclosed for exemplary purposes only, and are not meant to limit the scope of the present disclosure.

Second Embodiment

Referring to FIG. 1 to FIG. 4, FIG. 9 and FIG. 10, a second embodiment of the present disclosure provides a portable electronic device M for providing graphical information that is obtained by combining a temperature humidity index with a comfortability index, and the portable electronic device M includes a device main body M1, a signal control module M2, an information display module M3, a temperature and humidity sensing module M6, and a gas detection module M7.

More particularly, referring to FIG. 3 and FIG. 4, the signal control module M2 is disposed inside the device main body M1. In addition, the signal control module M2 has a plurality of key function execution commands, and the key function execution commands at least includes a top key function execution command 20U, a bottom key function execution command 20D, a left key function execution command 20L, and a right key function execution command 20R. For example, the device main body M1 includes a device casing (not labeled) and at least one circuit substrate 10 disposed inside the device casing, and the signal control module M2 is disposed on the circuit substrate 10 and electrically connected to the circuit substrate 10. In addition, the signal control module M2 can be a central processing unit (CPU), a digital signal process (DSP), a microprocessor unit (MPU), or a micro control unit (MCU), etc. However, the aforementioned details are disclosed for exemplary purposes only, and are not meant to limit the scope of the present disclosure.

Figure 9:
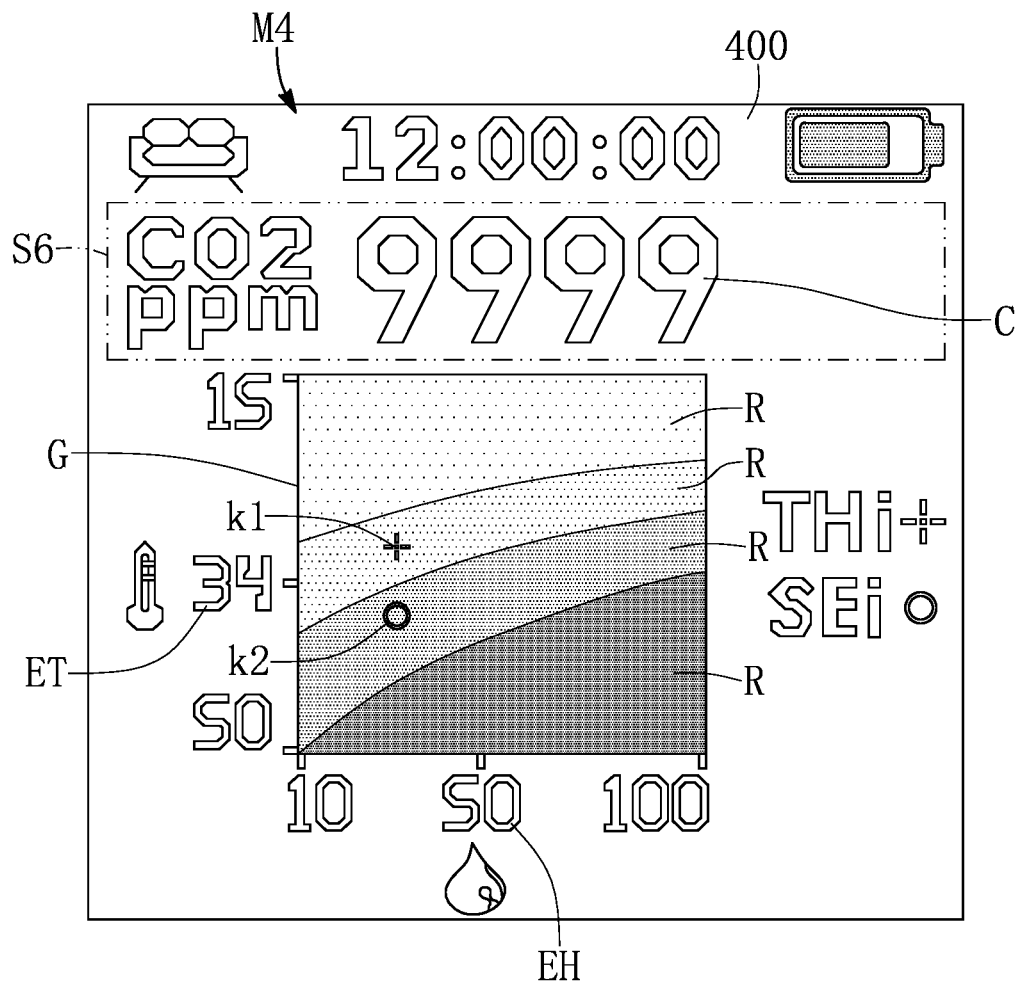
FIG. 9 is a schematic view of one of a plurality of information display images provided by an information display module of the portable electronic device according to a second embodiment of the present disclosure (i.e., a comfortability indicator is shown under a temperature and humidity indicator so as to be separate from the temperature and humidity indicator)

More particularly, referring to FIG. 2, FIG. 4 and FIG. 9, the temperature and humidity sensing module M6 is disposed inside the device main body M1 and electrically connected to the signal control module M2, and the temperature and humidity sensing module M6 can be configured for detecting temperature and humidity of an environment that surrounds the portable electronic device M so as to obtain an ambient temperature value ET and an ambient humidity value EH. For example, the temperature and humidity sensing module M6 is disposed on the circuit substrate 10 and electrically connected to the circuit substrate 10, and the temperature and humidity sensing module M6 can be a temperature and humidity sensor chip for concurrently detecting the temperature and the humidity of the environment that surrounds the portable electronic device M so as to concurrently obtain the ambient temperature value ET and the ambient humidity value EH. However, the aforementioned details are disclosed for exemplary purposes only, and are not meant to limit the scope of the present disclosure.

More particularly, referring to FIG. 2, FIG. 4 and FIG. 9, the gas detection module M7 is disposed inside the device main body M1 and electrically connected to the signal control module M2, and the gas detection module M7 can be configured to detect a gas concentration of a predetermined gas (i.e., an ambient gas) surrounding portable electronic device M (or the device main body M1) so as to obtain a gas concentration signal S3 (or a gas concentration value C). In addition, the information display module M4 can be configured to provide a display signal S6 according to the gas concentration signal S3 (that is to say, the information display module M4 can be configured to display the gas concentration value C of the gas concentration signal S3 that is detected by the gas detection module M7). For example, the gas detection module M7 is disposed on the circuit substrate 10 and electrically connected to the circuit substrate 10. In addition, the gas detection module M7 includes at least one of a $CO_2$ concentration sensor for obtaining a $CO_2$ concentration signal, an $O_2$ concentration sensor for obtaining an $O_2$ concentration signal, a CO concentration sensor for obtaining a CO concentration signal, a $CH_4$ concentration sensor for obtaining a $CH_4$ concentration signal, and an $NH_3$ concentration sensor for obtaining an $NH_3$ concentration signal. Therefore, a gas concentration of a predetermined gas (for example, the $CO_2$, $O_2$, CO, $CH_4$, or $NH_3$) surrounding the portable electronic device D can be detected by the gas detection module M7. However, the aforementioned details are disclosed for exemplary purposes only, and are not meant to limit the scope of the present disclosure.

Figure 10:
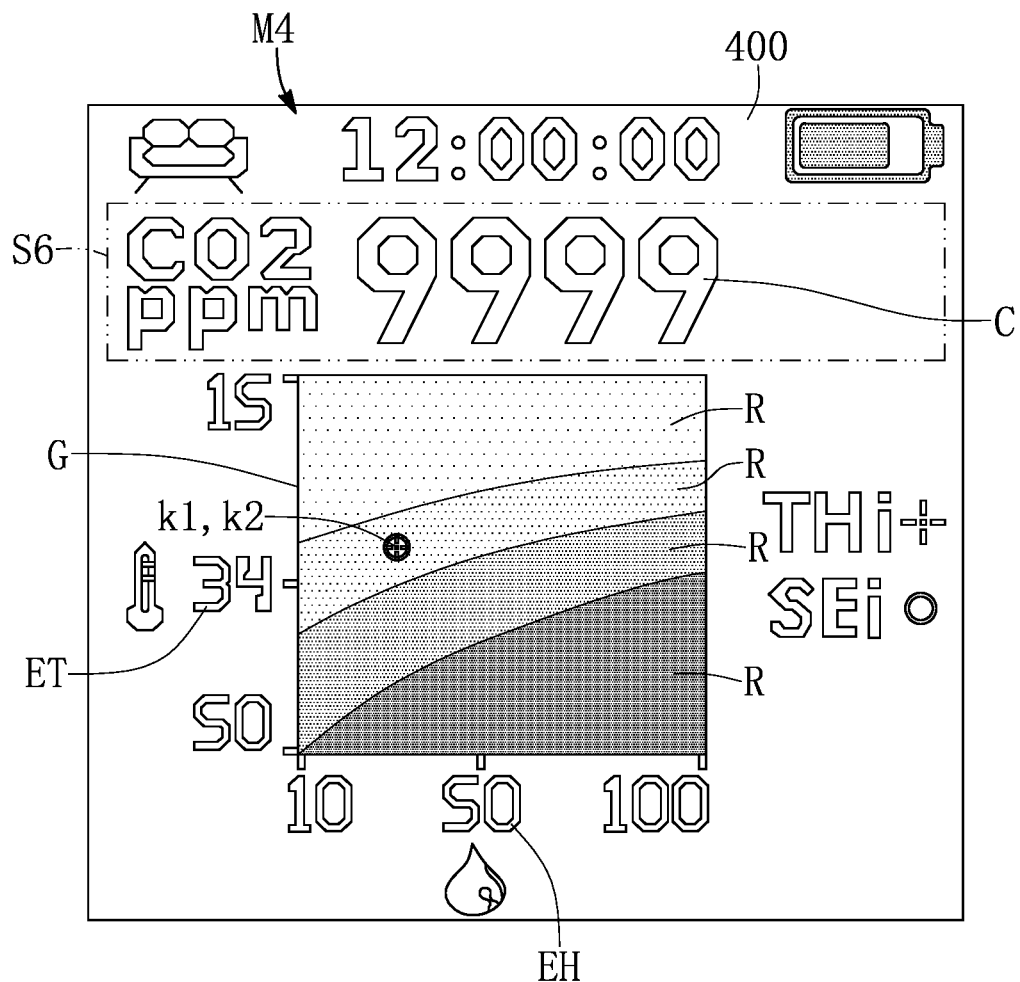
FIG. 10 is a schematic view of another one of the information display images provided by the information display module of the portable electronic device according to the second embodiment of the present disclosure (i.e., the comfortability indicator is shown upon the temperature and humidity indicator so as to contact or overlap with the temperature and humidity indicator)
Figure 11:
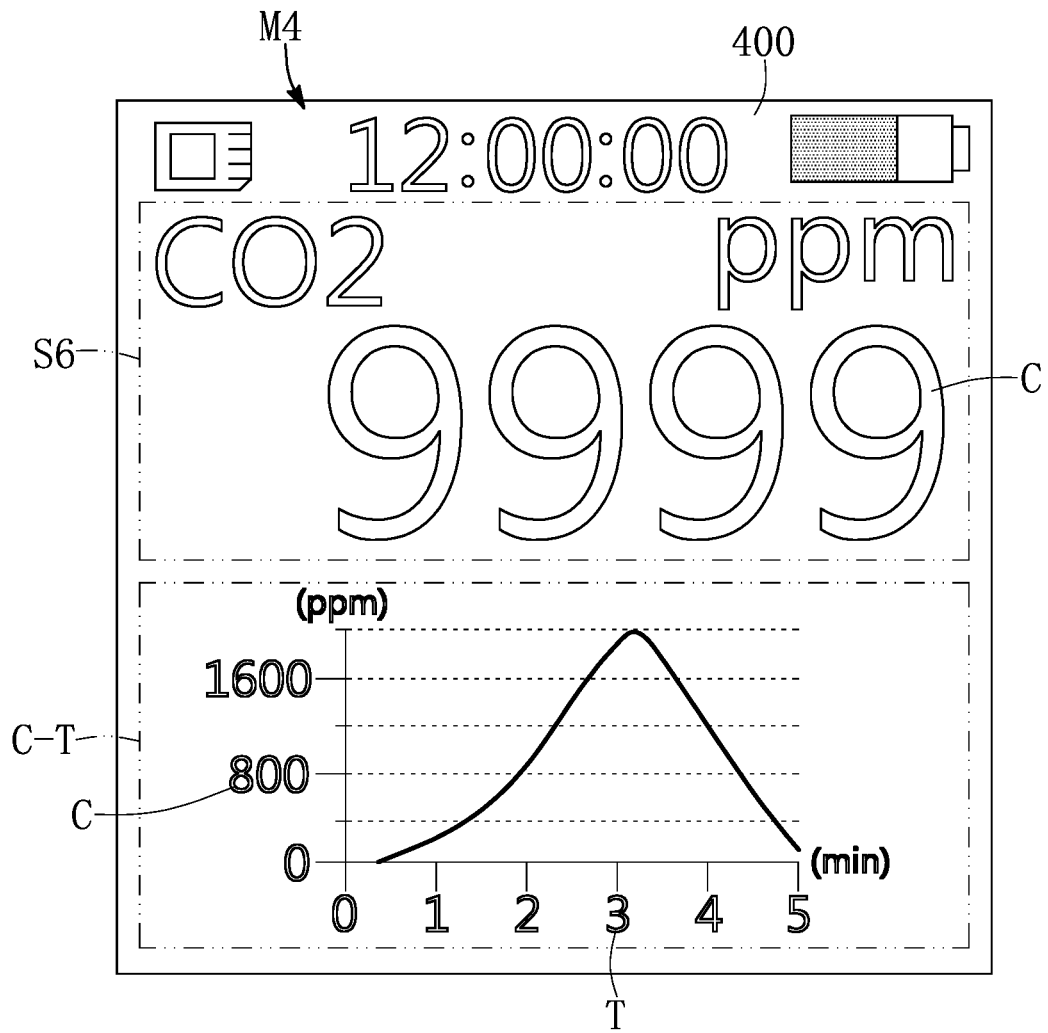
FIG. 11 is a schematic view of the information display module of the portable electronic device for displaying concentration and time trajectory information and a display signal according to a third embodiment of the present disclosure.

More particularly, referring to FIG. 4, FIG. 9 and FIG. 10, one of the information display images 400 that are provided by the information display module M4 has a temperature and humidity coordinate graph G, and a plurality of comfortability distribution areas R shown on the temperature and humidity coordinate graph G. In addition, the ambient temperature value ET and the ambient humidity value EH that are obtained by the temperature and humidity sensing module M6 can serve as a temperature and humidity indicator K1 (such as a cross indicator, and a location of the cross indicator can be obtained by respectively corresponding the ambient temperature value ET and the ambient humidity value EH with an X-axis and a Y-axis of the temperature and humidity coordinate graph G) shown on one of the comfortability distribution areas R, and the gas concentration value C that is obtained by the gas detection module M7 can serves as a comfortability indicator K2 (or a comfortness indicator such as a circular indicator) shown on one of the comfortability distribution areas R. It should be noted that the temperature and humidity indicator K1 and the comfortability indicator K2 can be shown on the same comfortability distribution area R (as shown in FIG. 9) or respectively shown on the two different comfortability distribution areas R (as shown in FIG. 10).

For example, the temperature and humidity indicator K1 and the comfortability indicator K2 can be shown or arranged along a same perpendicular line (or a same vertical line), and the comfortability indicator K2 can be shown under the temperature and humidity indicator K1 so as to be separate from the temperature and humidity indicator K1 (as shown in FIG. 9), or the comfortability indicator K2 can be shown on the temperature and humidity indicator K1 so as to contact or overlap with the temperature and humidity indicator K1 (as shown in FIG. 10). Therefore, as shown in FIG. 9, when the comfortability indicator K2 is shown under the temperature and humidity indicator K1 so as to be separate from the temperature and humidity indicator K1, a probability of a comfortability that is provided by the environment surrounding the portable electronic device M being affected by the predetermined gas is increased, so that the comfortability experienced by the user in the environment is reduced. In addition, as shown in FIG. 10, when the comfortability indicator K2 is shown upon the temperature and humidity indicator K1 so as to contact or overlap with the temperature and humidity indicator K1, the probability of the comfortability that is provided by the environment surrounding the portable electronic device M being affected by the predetermined gas is decreased, so that the comfortability experienced by the user in the environment is increased. However, the aforementioned details are disclosed for exemplary purposes only, and are not meant to limit the scope of the present disclosure.

Third Embodiment

Referring to FIG. 1 to FIG. 4, and FIG. 11 to FIG. 13, a third embodiment of the present disclosure provides a portable electronic device M, and the main difference between the third embodiment and the first and the second embodiment is as follows: in the third embodiment, the portable electronic device M further includes a temperature sensing module M8, a signal recording module M9, an audio generating module M10, a pressure sensing module M11, and a wireless transmission module M12.

More particularly, referring to FIG. 2, FIG. 3 and FIG. 4, the temperature sensing module M8 (such as an infrared array sensor) is disposed inside the device main body M1 and electrically connected to the signal control module M2, for capturing a thermal image of a predetermined object B so as to obtain thermal image information S2. In addition, the signal recording module M9 (such as a built-in memory or an external memory) is disposed inside the device main body M1 and electrically connected to the signal control module M2, for recording the gas concentration values C that are provided by the gas concentration signal S3, and recording the gas-measuring time points T that are respectively configured for obtaining the gas concentration values C by detecting the gas concentration of the predetermined gas.

More particularly, referring to FIG. 2, FIG. 3 and FIG. 4, the audio generating module M10 is disposed inside the device main body M1 and electrically connected to the signal control module M2, for providing an audio signal S4 (such as a warning sound) according to the gas concentration signal S3. In addition, the pressure sensing module M11 (such as a barometric pressure sensor) is disposed inside the device main body M1 and electrically connected to the signal control module M2, for detecting an atmospheric pressure of the environment surrounding the portable electronic device M so as to obtain height information S5. Moreover, the wireless transmission module M12 (or a wire transmission module) is disposed inside the device main body M1 and electrically connected to the signal control module M2, for wirelessly (or wiredly) transmitting information that is captured by the portable electronic device M to at least one electronic monitoring device P.

For example, when the gas concentration values C and the gas-measuring time points T match with each other to form concentration and time trajectory information C-T, the information display module M4 can be configured to display the concentration and time trajectory information C-T so as to determine a gas concentration change trend of the environment in which the user stays for a predetermined time range. In addition, the wireless transmission module M12 can be configured to wirelessly transmit the concentration and time trajectory information C-T to the at least one electronic monitoring device P. However, the aforementioned details are disclosed for exemplary purposes only, and are not meant to limit the scope of the present disclosure.

Figure 12:
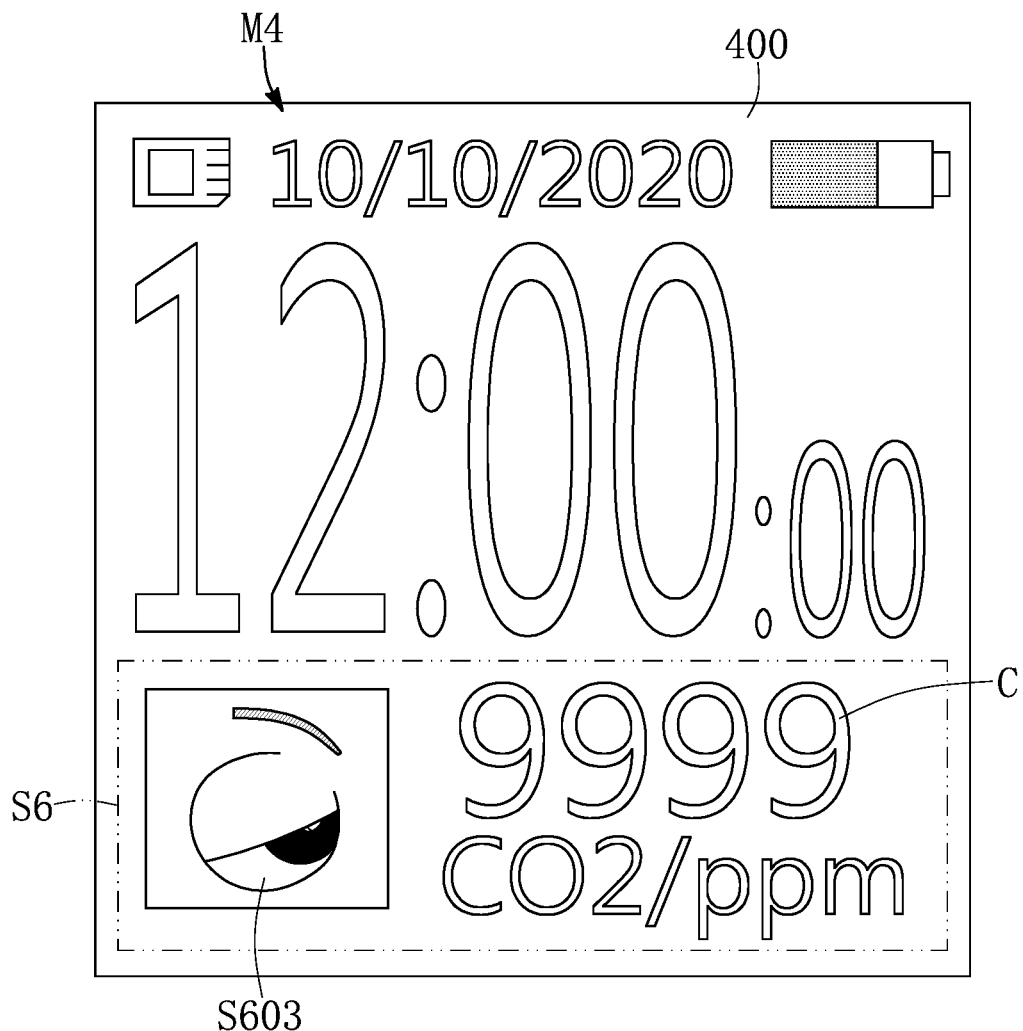
FIG. 12 is a schematic view of the information display module of the portable electronic device for displaying a third animation message and a gas concentration value according to the third embodiment of the present disclosure.
Figure 13:
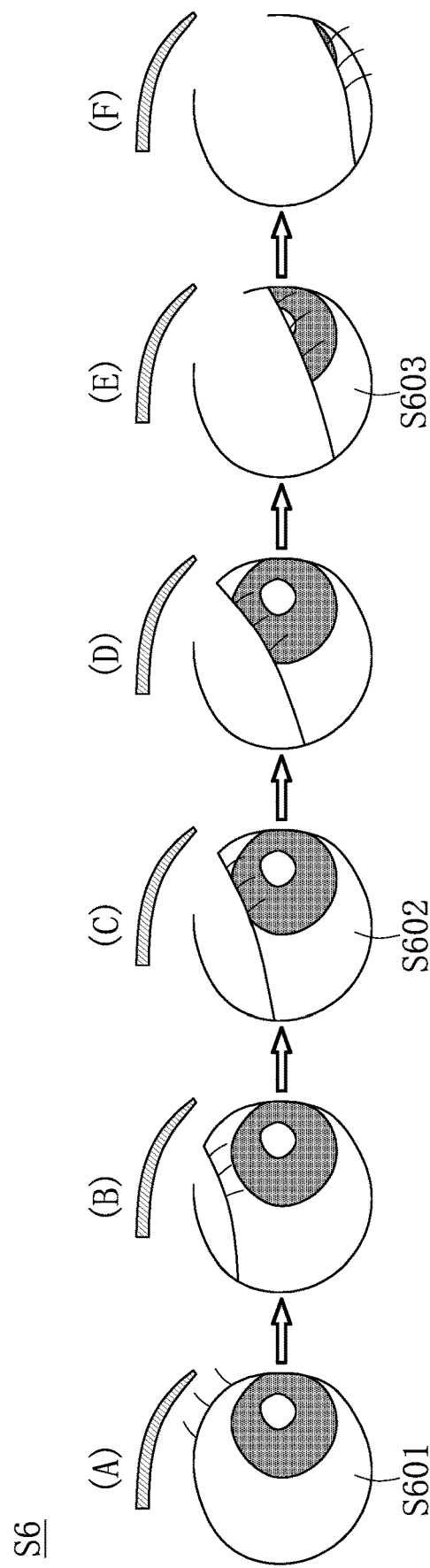
FIG. 13 is a schematic view of a plurality of blinking animations (such as a first, a second and a third blinking animation) presented by a display signal of the portable electronic device according to the third embodiment of the present disclosure.

For example, referring to FIG. 4, FIG. 12 and FIG. 13, when the gas concentration value C provided by the gas concentration signal S3 is less than a first preset value (for example, the $CO_2$ concentration is less than 1000 ppm), the display signal S6 generated by the information display module M4 includes a first color message (such as a safety color: green), a first animation message S601 (such as a first blinking animation (i.e., closing and opening eye once) as shown in (A) of FIG. 13), or a first combined message (such as a green first blinking animation). In addition, when the gas concentration value C provided by the gas concentration signal S3 is greater than the first preset value and less than a second preset value (for example, the $CO_2$ concentration is greater than 1000 ppm and less than 2000 ppm), the display signal S6 generated by the information display module M4 includes a second color message (such as a warning color: yellow), a second animation message S602 (such as a second blinking animation as shown in (C) of FIG. 13), or a second combined message (such as a yellow second blinking animation). Furthermore, when the gas concentration value C provided by the gas concentration signal S3 is greater than the second preset value (for example, the $CO_2$ concentration is greater than 2000 ppm), the display signal S6 generated by the information display module M4 includes a third color message (such as a dangerous color: red), a third animation message S603 (such as a third blinking animation as shown in FIG. 2 and (E) of FIG. 13), or a third combined message (such as a red third blinking animation). It should be noted that, as shown in FIG. 13, the blinking animations provided by the display signal S6 are respectively presented from (A) to (F) of FIG. 13, and the eye opening percentage of the blinking animation is gradually decreased from (A) to (F) of FIG. 13. That is to say, the eye opening percentage of the first blinking animation of the first animation message S601 is greater than the eye opening percentage of the second blinking animation of the second animation message S602, and the eye opening percentage of the second blinking animation of the second animation message S602 is greater than the eye opening percentage of the third blinking animation of the third animation message S603. However, the aforementioned description is merely an example, and is not meant to limit the scope of the present disclosure. However, the aforementioned details are disclosed for exemplary purposes only, and are not meant to limit the scope of the present disclosure.

Beneficial Effects of the Embodiments

In conclusion, in the portable electronic device M provided by the present disclosure, by virtue of the key control module M3 being electrically connected to the signal control module M2, the information display module M4 being electrically connected to the signal control module M2, for providing a plurality of information display images 400, the position detection module M5 being electrically connected to the signal control module M2, for detecting a placement orientation of the portable electronic device M so as to obtain an orientation signal S1, the key control module M3 including a plurality of functional switches 31 electrically connected to the signal control module M2, and a plurality of functional keys 32 respectively and selectively contacting the functional switches 31, and the information display module M4 including an information displayer 40 for displaying the information display images 400, and the signal control module M2 having a plurality of key function execution commands respectively corresponding to the functional keys 32, and the key function execution commands at least including a top key function execution command 20U, a bottom key function execution command 20D, a left key function execution command 20L, and a right key function execution command 20R, when the portable electronic device M is rotated so as to change the placement orientation of the information display module M4, a screen orientation of the information display image provided by the information display module M4 is changed following a change of the placement orientation of the information display module M4, and a corresponding relationship between the functional switch and the key function execution command is changed following the change of the placement orientation of the information display module M4.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:

1. A portable electronic device for use in different orientations, comprising:
    a device main body;
    a signal control module disposed inside the device main body;
    a key control module disposed on the device main body and electrically connected to the signal control module;
    an information display module disposed on the device main body and electrically connected to the signal control module, for providing a plurality of information display images;
    a position detection module disposed inside the device main body and electrically connected to the signal control module, for detecting a placement orientation of the portable electronic device so as to obtain an orientation signal;
    a temperature and humidity sensing module disposed inside the device main body and electrically connected to the signal control module, for detecting temperature and humidity of an environment surrounding the portable electronic device so as to obtain an ambient temperature value and an ambient humidity value; and
    a gas detection module disposed inside the device main body and electrically connected to the signal control module, for detecting a gas concentration of a predetermined gas surrounding the portable electronic device so as to obtain a gas concentration value and a gas concentration signal;
    wherein one of the information display images has a temperature and humidity coordinate graph and a plurality of comfortability distribution areas shown on the temperature and humidity coordinate graph, the ambient temperature value and the ambient humidity value that are obtained by the temperature and humidity sensing module serve as a temperature and humidity indicator shown on one of the comfortability distribution areas, and the gas concentration value that is obtained by the gas detection module serves as a comfortability indicator shown on one of the comfortability distribution areas;
    wherein the temperature and humidity indicator and the comfortability indicator are shown along a same perpendicular line, and the comfortability indicator is shown under the temperature and humidity indicator so as to be separate from the temperature and humidity indicator, or the comfortability indicator is shown upon the temperature and humidity indicator so as to contact or overlap with the temperature and humidity indicator;
    wherein the key control module includes a plurality of functional switches electrically connected to the signal control module, and a plurality of functional keys respectively and selectively contacting the functional switches, and the information display module includes an information displayer for displaying the information display images;
    wherein the signal control module has a plurality of key function execution commands respectively corresponding to the functional keys, and the key function execution commands at least includes a top key function execution command, a bottom key function execution command, a left key function execution command, and a right key function execution command;
    wherein, when the device main body is rotated so as to change the placement orientation of the information display module, a screen orientation of the information display image provided by the information display module is changed following a change of the placement orientation of the information display module, and a corresponding relationship between the functional switch and the key function execution command is changed following the change of the placement orientation of the information display module;

wherein, when the placement orientation of the information display module is changed through rotation of the device main body, a topmost one of the functional switches on the device main body is defined as a top functional switch for executing the top key function execution command, a bottommost one of the functional switches on the device main body is defined as a bottom functional switch for executing the bottom key function execution command, a leftmost one of the functional switches on the device main body is defined as a left functional switch for executing the left key function execution command, and a rightmost one of the functional switches on the device main body is defined as a right functional switch for executing the right key function execution command;

wherein, when the placement orientation of the information display module is changed through rotation of the device main body, a topmost one of the functional keys on the device main body is defined as a top functional key for executing the top key function execution command by pressing the top functional switch, a bottommost one of the functional keys on the device main body is defined as a bottom functional key for executing the bottom key function execution command by pressing the bottom functional switch, a leftmost one of the functional keys on the device main body is defined as a left functional key for executing the left key function execution command by pressing the left functional switch, and a rightmost one of the functional keys on the device main body is defined as a right functional key for executing the right key function execution command by pressing the right functional switch.

2. The portable electronic device according to claim 1, wherein the functional keys are separate from each other or combined to form a single key structure, and no character or pattern is formed on the functional key or a peripheral area around the functional key;

wherein the position detection module is an acceleration transducer or a gyroscope for detecting the placement orientation of the portable electronic device so as to obtain the orientation signal;

wherein the top key function execution command is an upward selection command, the bottom key function execution command is a downward selection command, the left key function execution command is a mode switching command, and the right key function execution command is an enter confirmation command;

wherein, when the top functional key is configured to press the top functional switch so as to execute the upward selection command, a plurality of different functional areas provided by the information display image are upwardly selected by the upward selection command;

wherein, when the bottom functional key is configured to press the bottom functional switch so as to execute the downward selection command, the different functional areas provided by the information display image are downwardly selected by the downward selection command;

wherein, when the left functional key is configured to press the left functional switch so as to execute the mode switching command, the information display images are selected by the mode switching command so as to display one of the information display images on the information display module;

wherein, when the right functional key is configured to press the right functional switch so as to execute the enter confirmation command, an enter confirmation signal is transmitted to the signal control module by control of the enter confirmation command.

3. The portable electronic device according to claim 1, wherein, when the comfortability indicator is shown under the temperature and humidity indicator so as to be separate from the temperature and humidity indicator, a probability of a comfortability that is provided by the environment surrounding the portable electronic device being affected by the predetermined gas is increased;

wherein, when the comfortability indicator is shown upon the temperature and humidity indicator so as to contact or overlap with the temperature and humidity indicator, the probability of the comfortability that is provided by the environment surrounding the portable electronic device being affected by the predetermined gas is decreased;

wherein the temperature and humidity indicator and the comfortability indicator are shown on the same comfortability distribution area or respectively shown on the two different comfortability distribution areas;

wherein the temperature and humidity sensing module is a temperature and humidity sensor chip for concurrently detecting the temperature and the humidity of the environment surrounding the portable electronic device so as to concurrently obtain the ambient temperature value and the ambient humidity value.

4. The portable electronic device according to claim 1, further comprising:

a temperature sensing module disposed inside the device main body and electrically connected to the signal control module, for capturing a thermal image of a predetermined object so as to obtain thermal image information;

an audio generating module disposed inside the device main body and electrically connected to the signal control module, for providing an audio signal according to the gas concentration signal;

a pressure sensing module disposed inside the device main body and electrically connected to the signal control module, for detecting an atmospheric pressure of the environment surrounding the portable electronic device so as to obtain height information; and a wireless transmission module disposed inside the device main body and electrically connected to the signal control module, for wirelessly transmitting information that is captured by the portable electronic device to at least one electronic monitoring device.

5. The portable electronic device according to claim 4, wherein the temperature sensing module is an infrared array sensor, and the pressure sensing module is a barometric pressure sensor;

wherein the gas detection module includes at least one of a $CO_2$ concentration sensor for obtaining a $CO_2$ concentration signal, an $O_2$ concentration sensor for obtaining an $O_2$ concentration signal, a CO concentration sensor for obtaining a CO concentration signal, a $CH_4$ concentration sensor for obtaining a $CH_4$ concentration signal, and an $NH_3$ concentration sensor for obtaining an $NH_3$ concentration signal, and the information display module is configured to display the gas concentration value of the gas concentration signal that is detected by the gas detection module;

wherein, when the gas concentration values and the gas-measuring time points match with each other to form concentration and time trajectory information, the information display module is configured to display the concentration and time trajectory information, and the wireless transmission module is configured to wirelessly transmit the concentration and time trajectory information to the at least one electronic monitoring device;

wherein the information display module is configured to provide a display signal according to the gas concentration signal;

wherein, when the gas concentration value provided by the gas concentration signal is less than a first preset value, the display signal generated by the information display module includes a first color message and a first animation message;

wherein, when the gas concentration value provided by the gas concentration signal is greater than the first preset value and less than a second preset value, the display signal generated by the information display module includes a second color message and a second animation message;

wherein, when the gas concentration value provided by the gas concentration signal is greater than the second preset value, the display signal generated by the information display module includes a third color message and a third animation message;

wherein an eye opening percentage of a first blinking animation of the first animation message is greater than an eye opening percentage of a second blinking animation of the second animation message, and the eye opening percentage of the second blinking animation of the second animation message is greater than an eye opening percentage of a third blinking animation of the third animation message.

6. A portable electronic device for use in different orientations, comprising:
a signal control module;
a key control module electrically connected to the signal control module;
an information display module electrically connected to the signal control module, for providing a plurality of information display images; a position detection module electrically connected to the signal control module, for detecting a placement orientation of the portable electronic device so as to obtain an orientation signal; and
a gas detection module electrically connected to the signal control module, for detecting a gas concentration of a predetermined gas surrounding the portable electronic device so as to obtain a gas concentration value and a gas concentration signal;
wherein the information display module is configured to provide a display signal according to the gas concentration signal;
wherein, when the gas concentration value provided by the gas concentration signal is less than a first preset value, the display signal generated by the information display module includes a first color message and a first animation message;
wherein, when the gas concentration value provided by the gas concentration signal is greater than the first preset value and less than a second preset value, the display signal generated by the information display module includes a second color message and a second animation message;

wherein, when the gas concentration value provided by the gas concentration signal is greater than the second preset value, the display signal generated by the information display module includes a third color message and a third animation message;

wherein an eye opening percentage of a first blinking animation of the first animation message is greater than an eye opening percentage of a second blinking animation of the second animation message, and the eye opening percentage of the second blinking animation of the second animation message is greater than an eye opening percentage of a third blinking animation of the third animation message;

wherein the key control module includes a plurality of functional switches electrically connected to the signal control module, and a plurality of functional keys respectively and selectively contacting the functional switches, and the information display module includes an information displayer for displaying the information display images;

wherein the signal control module has a plurality of key function execution commands respectively corresponding to the functional keys, and the key function execution commands at least includes a top key function execution command, a bottom key function execution command, a left key function execution command, and a right key function execution command;

wherein, when the portable electronic device is rotated so as to change the placement orientation of the information display module, a screen orientation of the information display image provided by the information display module is changed following a change of the placement orientation of the information display module, and a corresponding relationship between the functional switch and the key function execution command is changed following the change of the placement orientation of the information display module.

7. The portable electronic device according to claim 6,
wherein the functional keys are separate from each other, or combined to form a single key structure, and no character or pattern is formed on the functional key or a peripheral area around the functional key;
wherein the position detection module is an acceleration transducer or a gyroscope for detecting the placement orientation of the portable electronic device so as to obtain the orientation signal;
wherein the top key function execution command is an upward selection command, the bottom key function execution command is a downward selection command, the left key function execution command is a mode switching command, and the right key function execution command is an enter confirmation command;
wherein, when a topmost one of the functional keys is configured to press a topmost one of the functional switches so as to execute the upward selection command, a plurality of different functional areas provided by the information display image are upwardly selected by the upward selection command;
wherein, when a bottommost one of the functional keys is configured to press a bottommost one of the functional switches so as to execute the downward selection command, the different functional areas provided by the information display image are downwardly selected by the downward selection command;

wherein, when a leftmost one of the functional keys is configured to press a leftmost one of the functional switches so as to execute the mode switching command, the information display images are selected by the mode switching command so as to display one of the information display images on the information display module;

wherein, when a rightmost one of the functional keys is configured to press the rightmost one of the functional switches so as to execute the enter confirmation command, an enter confirmation signal is transmitted to the signal control module by control of the enter confirmation command.

8. The portable electronic device according to claim 6, further comprising:

a temperature and humidity sensing module electrically connected to the signal control module, for detecting temperature and humidity of an environment surrounding the portable electronic device so as to obtain an ambient temperature value and an ambient humidity value;

wherein one of the information display images has a temperature and humidity coordinate graph, and a plurality of comfortability distribution areas shown on the temperature and humidity coordinate graph, the ambient temperature value and the ambient humidity value that are obtained by the temperature and humidity sensing module serve as a temperature and humidity indicator shown on one of the comfortability distribution areas, and the gas concentration value that is obtained by the gas detection module serves as a comfortability indicator shown on one of the comfortability distribution areas;

wherein the temperature and humidity indicator and the comfortability indicator are shown along a same perpendicular line, and the comfortability indicator is shown under the temperature and humidity indicator so as to be separate from the temperature and humidity indicator, or the comfortability indicator is shown upon the temperature and humidity indicator so as to contact or overlap with the temperature and humidity indicator;

wherein, when the comfortability indicator is shown under the temperature and humidity indicator so as to be separate from the temperature and humidity indicator, a probability of a comfortability that is provided by the environment surrounding the portable electronic device being affected by the predetermined gas is increased;

wherein, when the comfortability indicator is shown upon the temperature and humidity indicator so as to contact or overlap with the temperature and humidity indicator, the probability of the comfortability that is provided by the environment surrounding the portable electronic device being affected by the predetermined gas is decreased;

wherein the temperature and humidity indicator and the comfortability indicator are shown on the same comfortability distribution area or respectively shown on the two different comfortability distribution areas;

wherein the temperature and humidity sensing module is a temperature and humidity sensor chip for concurrently detecting the temperature and the humidity of the environment surrounding the portable electronic device so as to concurrently obtain the ambient temperature value and the ambient humidity value.

9. The portable electronic device according to claim 6, further comprising:

a temperature sensing module electrically connected to the signal control module, for capturing a thermal image of a predetermined object so as to obtain thermal image information;

an audio generating module electrically connected to the signal control module, for providing an audio signal according to the gas concentration signal;

a pressure sensing module electrically connected to the signal control module, for detecting an atmospheric pressure of the environment surrounding the portable electronic device so as to obtain height information; and a wireless transmission module electrically connected to the signal control module, for wirelessly transmitting information that is captured by the portable electronic device to at least one electronic monitoring device.

10. The portable electronic device according to claim 9, wherein the temperature sensing module is an infrared array sensor, and the pressure sensing module is a barometric pressure sensor;

wherein the gas detection module includes at least one of a $CO_2$ concentration sensor for obtaining a $CO_2$ concentration signal, an $O_2$ concentration sensor for obtaining an $O_2$ concentration signal, a CO concentration sensor for obtaining a CO concentration signal, a $CH_4$ concentration sensor for obtaining a $CH_4$ concentration signal, and an $NH_3$ concentration sensor for obtaining an $NH_3$ concentration signal, and the information display module is configured to display the gas concentration value of the gas concentration signal that is detected by the gas detection module;

wherein, when the gas concentration values and the gas-measuring time points match with each other to form concentration and time trajectory information, the information display module is configured to display the concentration and time trajectory information, and the wireless transmission module is configured to wirelessly transmit the concentration and time trajectory information to the at least one electronic monitoring device.

* * * * *